United States Patent [19]

Bol et al.

[11] 4,161,366
[45] Jul. 17, 1979

[54] PROCESS AND APPARATUS FOR THE AUTOMATIC EXAMINATION OF EGGS FOR CRACKS OR PLACES OF FRACTURE IN THEIR SHELL

[75] Inventors: Johannes Bol, Heppenheim; Hans-Ulrich Freund, Friedrichsdorf, both of Fed. Rep. of Germany

[73] Assignee: Battelle-Institute e.V., Frankfurt am Main, Fed. Rep. of Germany

[21] Appl. No.: 768,601

[22] Filed: Feb. 14, 1977

[30] Foreign Application Priority Data

Feb. 13, 1976 [DE] Fed. Rep. of Germany ....... 2605721

[51] Int. Cl.² ............ G01N 33/08; G01N 21/32; G02B 27/17
[52] U.S. Cl. ...................... 356/56; 209/511; 250/236; 250/578; 350/6.9; 356/428; 356/240
[58] Field of Search .................. 356/52–68, 356/196–198, 201, 239–240, 36; 250/222 R, 223 B, 224, 562–563, 572, 236, 578, 553, 223 R; 350/6; 209/111.7 T, 510–511; 350/6.9

[56] References Cited

U.S. PATENT DOCUMENTS

| | | | |
|---|---|---|---|
| 2,044,981 | 6/1936 | Guttman | 209/111.7 |
| 3,069,553 | 12/1962 | Zoltanski | 356/240 |
| 3,072,798 | 1/1963 | Sick | 356/201 |
| 3,302,786 | 2/1967 | Conrad | 356/198 |
| 3,405,270 | 10/1968 | Briggs | 250/572 |
| 3,871,774 | 3/1975 | Murata | 356/239 |

FOREIGN PATENT DOCUMENTS 1141471 12/1962 Fed. Rep. of Germany ........... 356/240
494720 1/1976 U.S.S.R. .................................. 350/6

OTHER PUBLICATIONS

Chodakov, V. S., "Vibration Microphotography of Defects", Instruments & Experimental Techniques, vol. 18, 11, 12–75, pp. 1929–1931.
Stadelman, W. J., "Quality Identification of Shell Eggs", from Egg Science & Technology, edited by Stadelman et al., The AVI Pub. Co., 1973, pp. 26–31, 36–37.

*Primary Examiner*—John K. Corbin
*Assistant Examiner*—Wm. H. Punter
*Attorney, Agent, or Firm*—Fisher, Christen & Sabol

[57] ABSTRACT

A process and apparatus are disclosed for the automatic examination of eggs for cracks or fractured surface areas in their shells. The process includes the steps of directing light from at least one light source onto the egg, and detecting and measuring the intensity of the light emanating from the egg. Cracks or fractured surface areas in the egg shell will allow a greater intensity of light to emanate from the egg. Such relatively higher intensity is measured to determine if a crack or fracture exists. The apparatus consists of at least one light source, a device for rotating the egg, apparatus for moving the light beam over the surface of the egg shell, and a device for detecting the intensity level of the light emanating from the egg.

11 Claims, 7 Drawing Figures

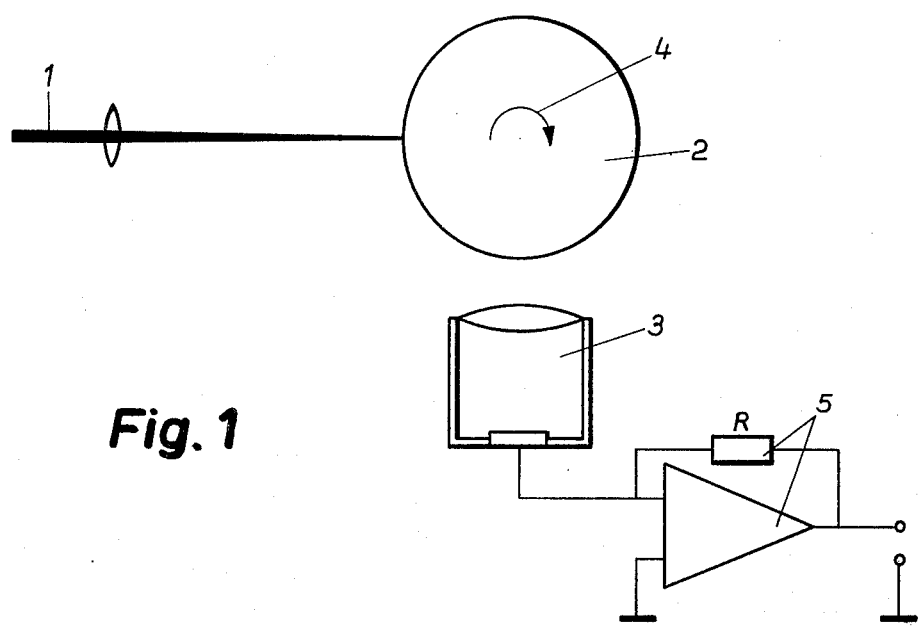
Fig. 1
Fig. 4
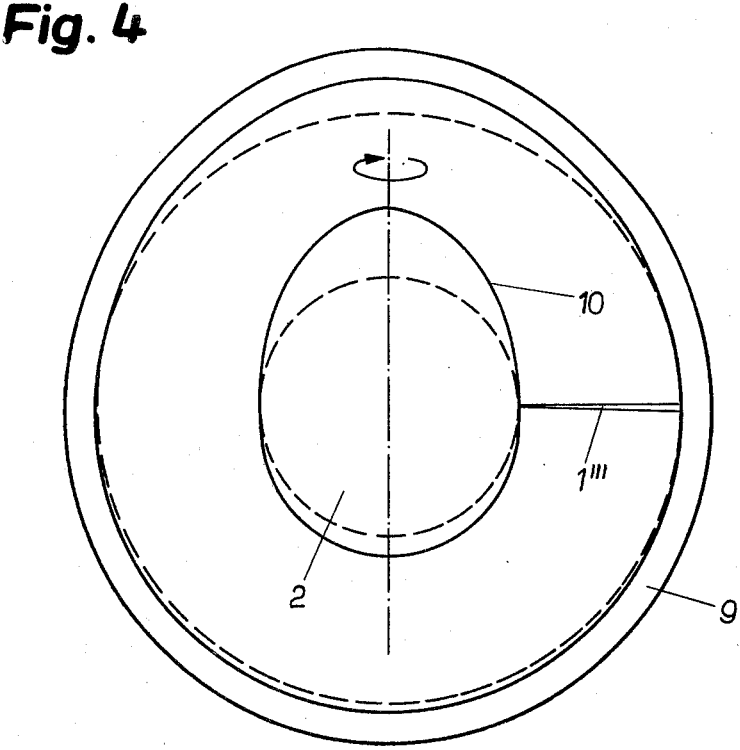

PROCESS AND APPARATUS FOR THE AUTOMATIC EXAMINATION OF EGGS FOR CRACKS OR PLACES OF FRACTURE IN THEIR SHELL

FIELD OF INVENTION

This invention relates to the field of detecting devices for detecting minute cracks or fractures in egg shells and a processes for using same.

DESCRIPTION OF PRIOR ART

Chicken eggs nowadays are sorted and packed in automatic installations according to classes of weight. During these processes the flawed eggs are sorted out so that they may be put to special use.

In the known installations, the eggs are examined visually in a light compartment for hair cracks or places of fracture. The eggs pass through the light compartment in several rows side by side, while they rotate slowly. Depending on the capacity of the installation, the compartment is occupied by one or more persons and up to 12,500 eggs can be controlled per hour by one person. The fraction of flawed eggs normally is between 5 and 15%.

One disadvantage of this method for the detection of flawed eggs, is that the expenditure in personnel is relatively high and that, moreover, in practice only about half of the flawed eggs are discovered.

It has also already been known that a hair crack in the shell of an egg changes the elastic and acoustic characteristics of the shell. Therefore, it is known that a flaw can be recognized from the type of sound which develops in case of tapping such as with the help of a second egg. The change in the elastic characteristics can be discovered with the help of a small hammer, which, after striking the egg on places with hair cracks will strike back less far than from places which are not cracked (Dutch patent application No. 28 64 85). Both processes are cumbersome, slow and relatively expensive due to the manpower required. Whenever an egg is put into low frequency oscillation by means of a vibrator, a damping of the vibration on the flawed places which can be detected either from the reaction on the vibration generator, or by scanning the vibrating egg with a vibration detector. The vibration generator or detector, however, must be placed near the crack. The transmission behavior of the egg for ultrasonic vibrations also changes as a result of cracks in the shell; at the same time it is not necessary that the hair crack be in the immediate vicinity of the sound generator or sound receiver.

The development of detecting processes on the basis of the previously mentioned phenomena however fails in practice because of the fact that the transmitting behavior even in the case of perfect egg shells varies considerably from egg to egg and that it is not possible to fix a threshold value, the exceeding of which would be characteristic for flawed eggs.

SUMMARY OF THE INVENTION

Therefore, the invention is based on the task of developing a process with the help of which the sorting out of flawed eggs can be accomplished automatically. For this purpose a measuring process has been developed which allows flawed eggs to be detected with certainty, sufficiently quickly, and without endangering the eggs. The apparatus for carrying out the process is constructed robustly and simply so that a continuous supervision by qualified personnel is not required. All these factors have a favorable effect on the profitability of the process.

This task has been solved by a process wherein the egg is scanned with a light beam and the intensity of the light penetrating into the egg is measured. The light penetrating into the egg is scattered all around evenly within the egg and then measured outside the egg as scattered light. From the temporal course of the measured light intensity, a signal for the discovery of particularly light permeable places of fracture can be deduced.

Following an advantageous embodiment of the invention, the egg, is rotated and the light beam is guided across the egg shell, running around an axis perpendicular to the axis of rotation of the egg preferably on a scanning path including both ends of the egg. This can be accomplished with the help of a fixed source of light in connection with a rotating reflecting mirror, which, in turn, guides the light, via two annular, oval mirrors adapted to the contour of the egg, over the egg shell along the scanning path.

In another embodiment instead of a single light source with a rotating reflecting mirror, the scanning may be carried out with a large number of light beams which are directed perpendicularly onto various places of the egg shell and which then are switched on and off alternatingly at a high impulse frequency as compared to the rotational speed of the egg.

A single laser or several lasers may be used as the light sources. On the other hand however, it will be advantageous in many cases to make use of light diodes as sources of light, preferably light diodes irradiating in the near infrared range, such as luminescent diodes or laser diodes.

The light penetrating into the egg through the shell and at a higher intensity, through a crack or a fracture and which is scattered inside the egg, may be measured according to an embodiment of the invention with a photodetector directed onto the egg.

In another embodiment of the invention, the egg is illuminated and the light emerging from the egg is projected onto one or more diaphragms behind which a photodetector has been disposed. The diameter of the diaphragm is adapted to the width of the projection of the cracks or places fracture that are to be discovered. In the place of the diaphragm with a connected photodetector, the emerging light can also be projected directly on photodetectors which, in turn, should correspond in their diameter to the width of the reproduction of the hair crack.

In each embodiment of the above mentioned detection processes, the egg is rotated and one or more optical scanning arrangments, directed to various places of the egg shell, are used.

Provision has also been made to illuminate the egg and then to vibrate the egg shell mechanically, whereby the light emerging from the egg is measured and is checked to see if there is any light present modulated with the frequency of the mechanical vibrations. In this case use is made of the physical phenomenon that the width of the gap of a hair crack changes with the vibrating frequency of the coupled vibrator. Whenever a part of the light emerging from the egg is modulated with the mechanical vibration, then this indicates the presence of hair cracks or places of fracture in the egg shell. The light modulated correspondingly with the vibration stimulation, may be separated without difficulty by electronic frequency filtering of the photodetector signal from the basic background of the constant light produced by the light band, with which the rotating egg is illuminated along its rotational axis.

Further characteristics, advantages and possibilities of use of the invention will follow from the following description.

BRIEF DESCRIPTION OF THE DRAWING

FIG. 1 is a schematic diagram of a first embodiment of the invention.

FIG. 4 is a sectional view cut along the lines IV—IV in FIG. 3.

FIG. 7 is a side view of an alternative embodiment of the instant invention.

DETAILED DESCRIPTION OF PREFERRED EMBODIMENTS

In the embodiment according to the invention following FIG. 1, a narrow focused beam of light 1 is directed onto the surface (shell) of the egg 2 that is to be examined for hair cracks and places of fracture. A part of the light penetrates the shell into the inside of the egg and is uniformly scattered, thereby causing the egg to appear lit up. A part of this scattered light is detected by a photodetector 3 and is examined for its intensity.

Figure 2:
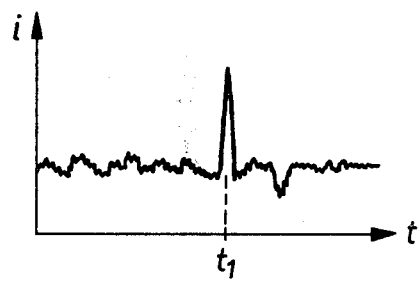
FIG. 2 is a graph showing the variation of emitted light intensity versus time according to the embodiment of FIG. 1.

Whenever the egg shell with the focused light beam 1 is scanned, by rotating the egg 2 in the direction of the arrow 4 around the indicated longitidinal axis of said egg, the signal of photodetector 3 (photo stream) scanned at the exit of the amplifier step 5 fluctuates in correspondence with the permeability of the egg shell. Whenever the light beam 1 strikes a crack in the shell of the egg 2, then a larger part of the light will reach the inside of said egg through the crack gap and the scattered light determined by the detector 3 and the photo stream i, shown in FIG. 2, will rise. One will obtain signal pulses which can be differentiated both in their amplitude as well as in their rising and falling time and in their duration form the signal fluctuations occuring at the perfect egg shell. In FIG. 2 the course of the signal over the time as in the case of the arrangement according to FIG. 1, is shown and the steeply rising signal at the time t1 clearly points to a crack in the egg shell.

The signal-to-noise ratio of the signal is the greatest whenever the diameter of the scanning light ray 1 corresponds to the width of the gap of the detecting hair crack. Furthermore, it is advantageous in regard to the signal-to-noise ratio, that the beam of light hits the egg shell as perpendicularly as possible. Most hair cracks may be securely detected with a light beam of 100 μm. The very finest hair cracks require a focusing of the light beam on a diameter up to 20 μm. At the same time it is favorable that the aperture of the focused light beam is as small as possible, the light beam therefore is slender, since in that case on the one hand, the diameter of the light beam changes little along the stretch corresponding to the thickness of the egg shell and because on the other hand in this case the focusing on the surface of the egg is not critical, since the focus has a great depth.

A slender, finely focused beam of light with an intensity sufficient for pratical application can be realized by using a light beam emanating from a laser. In the following table a few values of the diameter of the focus determined by defraction of light, of the focused beam of a helium neon laser with a wave length of $=0.63$ um and an emergence diameter of the light beam of 0.75 mm is shown in dependence on the focal length of the focusing optic system or on the aperture of the focusing light beam:

| Focal length of the focusing lens (mm) | 80 | 40 | 20 | 10 |
|---|---|---|---|---|
| opening relationship of the focused beam | 0.009 | 0.019 | 0.038 | 0.075 |
| diameter of the focus (μm) | 164 | 82 | 41 | 20.5 |

With a laser the desirable focus diameters, very slender light beams, may be realized without any loss of light intensity. The monochromacy and coherence of the laser light are not utilized directly in the detection process according to the invention. In principle therefore, even incoherent light sources such as light bulbs, luminescent diodes, mercury high pressure lamps, etc., may be used as the light source.

Figure 3:
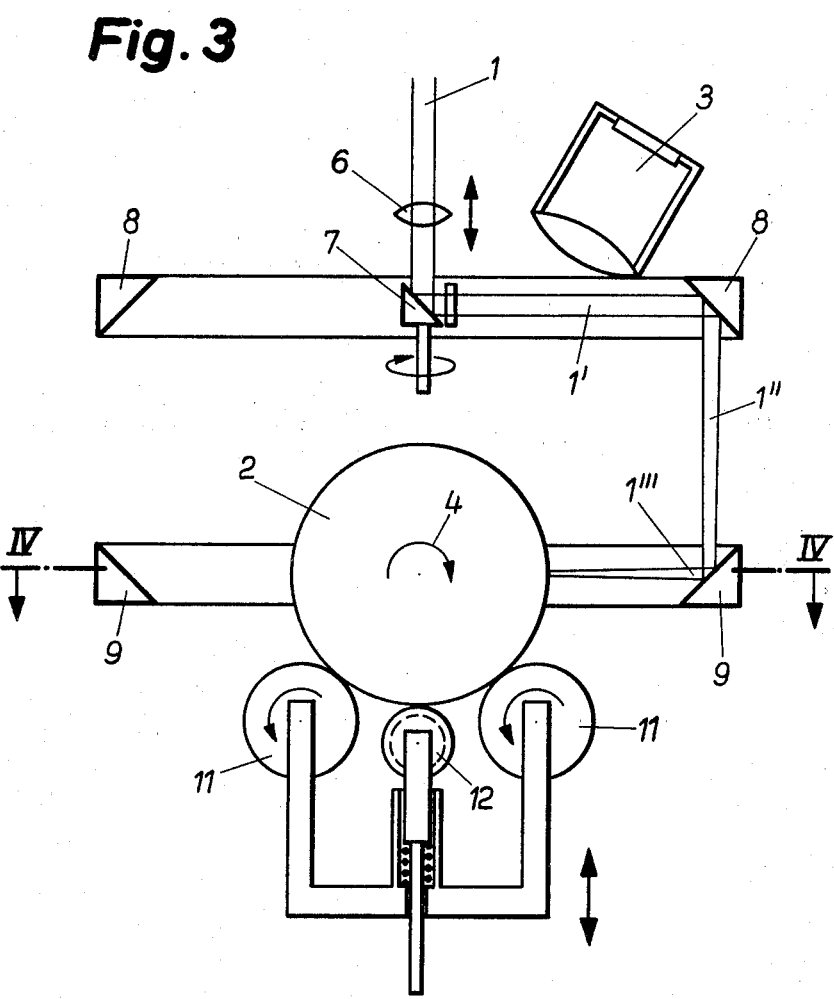
FIG. 3 is a top view, partly in section, showing the details of the embodiment of FIG. 1.

According to the embodiment of the invention shown in FIG. 3, the light beam 1 is guided both in the longitudinal direction as well as in the transverse direction on revolving scanning paths over the entire shell of the egg. For this purpose, as in FIG. 1, the egg is again put in rotation in the direction of the arrow 4 and the collimated light beam 1, in this case a laser light beam, is directed through lens 6, onto a rotating reflecting mirror 7. The direction of rotation is around an axis lying in the plane of the drawing is indicated in FIG. 3 by an arrow near the mirror 7. A revolving focused light beam 1', 1'', 1''' is produced by way of two annular, approximately oval, reflecting mirrors 8, 9 adapted to the contour of the egg, which light beam scans the shell of the egg 2 along its longitudinal periphery. At the same time, the beam runs on a scanning path including both ends of the egg, which path corresponds approximately to the contour in FIG. 4. The principle embodiment of the annular and oval mirrors 8, 9 can be recognized particularly clearly from FIG. 4.

In order to compensate for the astigmatism created by the curvature of the annular mirrors 8, 9, a cylinder lens participating with the mirror 7 in the rotation may be inserted into the path of the rays.

The egg 2 rotates on the rollers 11, around its longitudinal axis. As a result of that, the entire egg shell is scanned by the light beam which, as described, rotates under the influence of the rotating mirror 7 and the annular mirrors 8, 9 on longitudinal paths. The scanning paths developing in this manner across the two points or ends of the egg run across its largest periphery. The mutual distance of the individual scanning paths depends at the same time on the speed of rotation of the egg rotating in the direction of the arrow 4 and on the speed of rotation of the reflecting mirror 7. Whenever the egg rotates at 1 Hz and the scanning beam at 50 Hz, then the egg is scanned in 0.5 s on paths which are about 3 mm apart from one another at the greatest periphery around the longitudinal axis.

The detector 3 in FIG. 3 can be directed to every area of the surface of the egg outside of the scanning plane. In the case of the arrangement of the detector 3 below the egg 2, there is the danger of contamination of eggs leaking out, and therefore in a preferred embodiment of the invention, the detector 3 was disposed above the egg 2.

The rollers 11 also serve for the purpose of lifting the egg independently of its size precisely into the measuring plane. For this purpose, the size of the egg 2 is determined by means of an additional scanning roll 12 and the relative position between the egg and the scanning beam is adjusted automatically. It is also possible to shift the lens 6 corresponding to the size of the pertinent egg determined with the scanning roll 12 in such a way that the focus will revolve essentially on the surface of the egg both in the case of large as well as small eggs.

Figure 5:
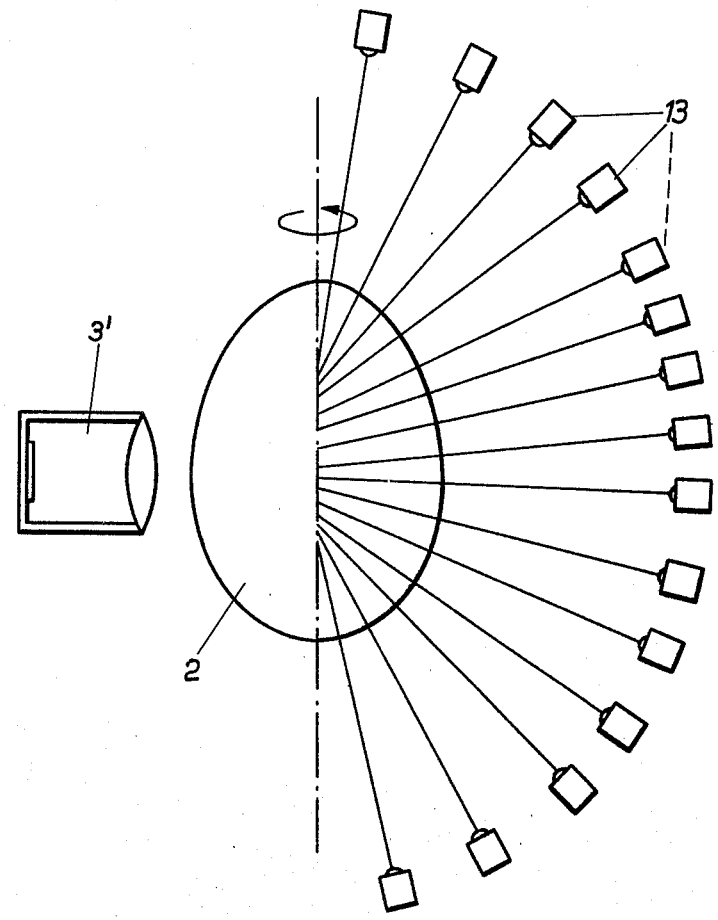
FIG. 5 is a schematic diagram of a second embodiment of the invention.

The process according to the invention can also be carried out with the arrangement according to FIG. 5. In this case instead of a revolving scanning beam, as had been explained on the basis of FIGS. 3 and 4, the scanning may be carried out with the help of a multiplicity of light beams which strike the egg shell in a direction perpendicular to the egg surface as close as possible and which are switched on and off in succession. The scanning beams must indeed not be in operation simultaneously, since the light of a scanning beam scattered on a hair crack would then not have a sufficient signal-to-noise ratio as compared to the light of the other scanning beams scattered on the perfect shell of the egg 2.

Preferably, semiconductor luminescent diodes, better still semiconductor laser diodes, which may produce short light pulses of high impulse recurrence frequency are used as light sources 13 in case of the measuring arrangement according to FIG. 5. With corresponding shift registers, the light sources 13 in the case of this method are lit temporarily in close succession, so that at any one point in time always only one source of light illuminates and each indiviudal source of light 13 delivers light impulses at a scanning ratio corresponsing to the number of light sources.

The egg in this case is again located on an arrangement with rollers 11, 12 as shown in FIG. 3, so that it can be put into rotation at the desired speed of rotation. Whenever the speed of rotation amounts to about 1 Hz, then in the case of a hair crack a signal impulse develops at the photodetector 3' with a duration of about 500 µs at the largest periphery around the longitudinal axis with a continuously illuminating scanning beam. In the case of intermittent operation of the pertinent light sources 13, this signal impulse should be covered up at least by five, better still by ten light impulses; this corresponds to a pulse recurrence frequency of 10-20 kHz. In the case of 20 light sources, i.e. a scanning ratio of 1:20, each individual light pulse is about 2.5 to 5 µs long. The photodetector 3' must respond quickly enough so that these individual light pulses can be reproduced undampened; this can be realized with the customary photodetectors.

Figure 6:
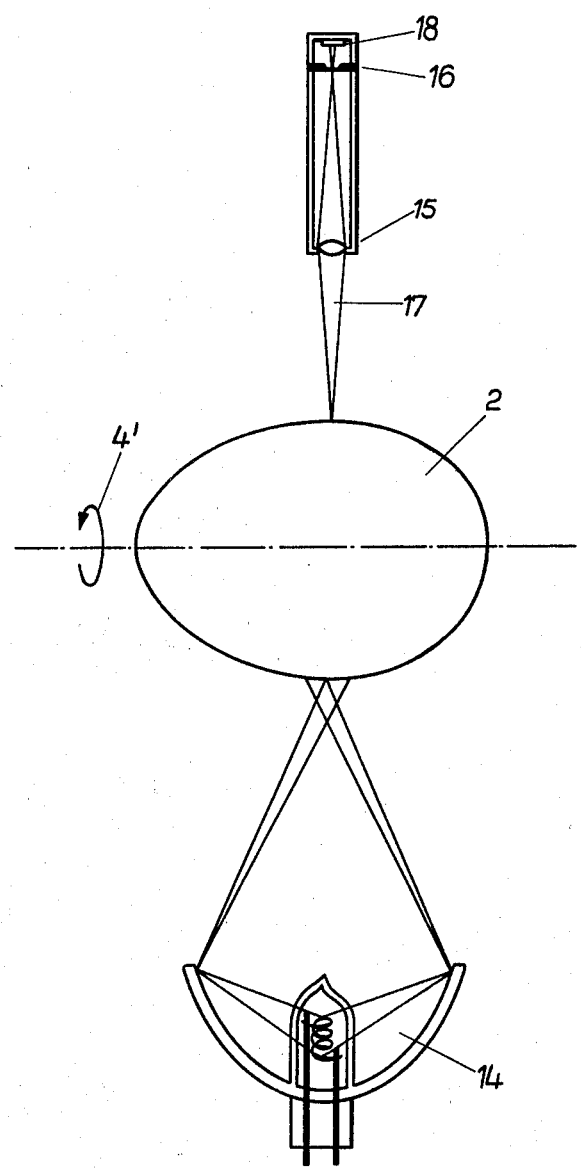
FIG. 6 is a schematic diagram of a third embodiment of the invention.

It has furthermore been provided within the scope of the present invention to also exploiting the reversal of the previously explained optical detection system, for the detection of the hair cracks or places of fracture in the egg shell. A corresponding arrangement has been reproduced in FIG. 6. The egg 2, again in this case rotating around its longitudinal axis in the direction of the arrow 4', is illuminated at the same time from one side over a large surface with a light source 14. Light penetrating into the egg 2 and scattered all around in the inside of the egg, then again emerges on hair cracks at a higher intensity. The egg shell in this case is projected onto a disc diaphragm 16 with an optical arrangement 15 which resembles a microscope lens, the diameter of the diaphragm corresponds to the expected width of the image of a hair crack in the egg shell. The light penetrating through the diaphragm 16—the projecting light beam is designated in FIG. 6 in its totality as element 17—is picked up by a photodetector 18 disposed directly behind the diaphragm 16. Whenever the bright picture of a hair crack runs across the diaphragm 16, then a signal impulse develops on the photodetector 18, the amplitude and the course of time of which may be utilized as criteria for the existence and dimensions of a crack; the course of the signal corresponds to that in FIG. 2. In the case of this arrangement one can use several optical scanning arrangements consisting of the elements 15, 16 and 18, at the same time, since no mutual influencing of the output signals occurs.

For the embodiment of the invention which has been mentioned already, in the case of which a vibrator 20 stimulates the illuminated egg shell 2 into mechanical vibrations and then in the case of the presence of a crack, modulated light can be determined with the frequency of this mechanical vibration, various possibilities of realization are conceivable. Since for this purpose one will fall back to known construction elements, it is not necessary to explain this embodiment in more detail.

Which of the described variations of the process of the invention are the most favorable ones, depends among other things on the already existing sorting and packaging installations within the scope of which an arrangement for carrying out the process of the invention is to be inserted. In this case however, the required speed of operation and the precision with which the existence and the size of the cracks or places of fracture in the egg shell are to be determined, is important.

What is claimed is:

1. A process for detecting cracks or fractures in an egg shell comprising the steps of:
    (a) rotating the egg about its longitudinal axis;
    (b) focussing at least one beam of light from a light source;
    (c) directing the focussed light beam onto a rotatable mirror;
    (d) rotating the rotatable mirror such that the light beam scans the egg shell along circumferential paths including both ends of the egg; and
    (e) detecting and measuring the intensity of light emanating from the egg such that cracks or fractures can be located, the light emanating from the egg at a higher intensity when the light beam enters the egg through a crack or fracture.

2. The process of claim 1 wherein the source of the light beam is stationary and comprising the additional steps of:
    (a) reflecting the light beam from said rotatable mirror onto a first annular stationary mirror;
    (b) reflecting the light beam from said first annular stationary mirror onto a second annular stationary mirror;
    (c) reflecting the light beam from said second annular stationary mirror onto the egg shell.

3. Apparatus for detecting cracks or fractures in an egg shell comprising:
    (a) means to rotate the egg about its longitudinal axis;

(b) means to focus at least one beam of light from at least one light source;

(c) a rotatable mirror which reflects the light beam onto said egg;

(d) means to rotate said rotatable mirror such that the light beam scans the egg shell along circumferential paths including both ends of the egg; and (e) means to detect and measure the intensity of light emanating from the egg, said intensity being higher if the focussed light beam enters the egg through a crack or fracture.

4. Apparatus of claim 3 further comprising:

(a) a first annular, stationary mirror which reflects the light beam reflected by the rotatable mirror;

(b) a second annular stationary mirror which reflects the light beam reflected by said first annular stationary mirror onto said egg shell; and (c) means to rotate said rotatable mirror such that said light beam scans the egg shell generally parallel to its axis of rotation.

5. Apparatus of claim 4 wherein the second annular stationary mirror is disposed in the plane of the axis of rotation of the egg.

6. A process for detecting cracks or fractures in an egg shell comprising the steps of:

(a) rotating the egg about its longitudinal axis;

(b) focussing beams of light from a plurality of light sources;

(c) directing the plurality of focussed light beams perpendicularly onto said egg shell, the beams oriented so as to effectively cover the surface of the egg shell;

(d) scanning the egg shell with said focussed light beams; and, (e) detecting and measuring the intensity of light emanating from the egg such that cracks or fractures can be located, the light emanating from the egg at a higher intensity when the light beam enters the egg through a crack or fracture.

7. The process of claim 6 wherein the light beams are sequentially switched on and off and the frequency of switching on and off each light beam is higher than the rotational frequency of the egg.

8. Apparatus for detecting cracks or fractures in an egg shell comprising:

(a) means to rotate the egg about its longitudinal axis;

(b) a plurality of light sources;

(c) means to sequentially switch each source on and off;

(d) means to focus means of light from said light sources;

(e) means to direct said focussed, light beams perpendicularly onto said egg shell;

(f) means to scan the egg shell with said focussed light beam; and (g) means to detect and measure the intensity of light emanating from the egg, said intensity being higher if the focussed light beam enters the egg through a crack or fracture.

9. Apparatus of claim 8 wherein the plurality of light sources are oriented in a plane parallel to the axis of rotation of the egg.

10. Apparatus of claim 8 wherein the frequency of sequentially switching each ligh source on and off is greater than the frequency of rotation of the egg.

11. Apparatus of claim 8 wherein the plurality of light sources are oriented such that each source directs a light beam onto a different area of the egg shell.

* * * * *

UNITED STATES PATENT OFFICE
CERTIFICATE OF CORRECTION

Patent No. 4,161,366            Dated July 17, 1979

Inventor(s) Johannes Bol and Hans-Ulrich Freund

It is certified that error appears in the above-identified patent and that said Letters Patent are hereby corrected as shown below:

In the heading, item 73, cancel the designated assignee and insert therefor:

--Staalkat B.V., 14 Hofstraat, Nl - Aalten, Netherlands--

[SEAL]

Signed and Sealed this

Fifteenth Day of January 1980

*Attest:*

SIDNEY A. DIAMOND

*Attesting Officer*      *Commissioner of Patents and Trademarks*